United States Patent
Chao

(10) Patent No.: US 8,020,785 B2
(45) Date of Patent: Sep. 20, 2011

(54) AROMATIC DEODORANT

(75) Inventor: I-Te Chao, Yonghe (TW)

(73) Assignee: KYVAS International Co., Ltd., Taipei County (TW)

( * ) Notice: Subject to any disclaimer, the term of this patent is extended or adjusted under 35 U.S.C. 154(b) by 0 days.

(21) Appl. No.: 12/550,114

(22) Filed: Aug. 28, 2009

(65) Prior Publication Data

US 2011/0052450 A1    Mar. 3, 2011

(51) Int. Cl.
*A61L 9/12* (2006.01)
*A61L 9/04* (2006.01)
(52) U.S. Cl. .................. 239/58; 239/53; 239/55; 239/56
(58) Field of Classification Search .................... 239/34, 239/36, 44, 53–59, 152, 154, 600
See application file for complete search history.

(56) References Cited

U.S. PATENT DOCUMENTS

| 4,258,004 | A | * | 3/1981 | Valenzona et al. | 422/123 |
| 4,549,693 | A | * | 10/1985 | Barlics | 239/58 |
| 4,944,455 | A | * | 7/1990 | Haust et al. | 239/59 |
| 2007/0207067 | A1 | * | 9/2007 | Zarembinski | 422/123 |
| 2008/0061162 | A1 | * | 3/2008 | Zarembinski | 239/59 |

* cited by examiner

*Primary Examiner* — Darren W Gorman
(74) *Attorney, Agent, or Firm* — Leong C. Lei

(57) ABSTRACT

An aromatic deodorant includes a first cover, a second cover and a scent device. An interior of the first cover is extended outward with a fixing element, an interior of the second cover is extended outward with a fixing seat to pivot the fixing element, the scent device is transfixed at the fixing element and is fixed by the fixing seat, and a scent dissipated by the scent device is released outside by convection through air vents on the first cover. When stopping dissipating the scent, a user only needs to rotate the first cover and the second cover through pivoting of the fixing element and the fixing seat, and uses the isolation plate on the second cover to block the air vents. Thus, the deodorant can be put in any space where a bad smell needs to be removed and not only saves space but is used very conveniently.

2 Claims, 7 Drawing Sheets

400
AROMATIC DEODORANT

BACKGROUND OF THE INVENTION a) Field of the Invention

The present invention relates to a device for removing bad smell and more particularly to an aromatic deodorant which is small in size and can control release of a scent to remove the bad smell.

b) Description of the Prior Art

Everyone must be full of various scents in each daily life and different scents will bring in a pleasant mood or a gloomy touch. When being in the pleasant mood in a long time, one can have a stable emotion and in a same time, ambient atmosphere can be changed. Therefore, all kinds of devices which can change scents depending on different places are shown up in markets and a place where the bad smell can be formed most easily in the daily life is a shoe cabinet which carries all kinds of shoes. As the shoes are one of clothing that people wear the longest time each day, and when feet are smothered in the shoes for a long time, it will be very easy to result in the uncomfortable bad smell, following inaction and increase of moisture and temperature. Accordingly, in order not to allow the feet to sweat too easily and to keep dry in the shoes, some people will spray baby powder uniformly in the shoes or put insoles woven by hay into the shoes, so as to decrease the unbearable bad smell in the shoes.

However, when the aforementioned methods that improve the bad smell in the shoes are used, following issues and shortcomings actually exist for improvement:

1. Although the aforementioned baby powder can effectively improve the generation of the bad smell after being sprayed, griminess in the shoes and on the feet can be quickly increased that it can be very inconvenient in cleaning.
2. On the other hand, the effect of reducing the bad smell using the insoles woven by hay is not very significant and when these kinds of insoles are not replaced timely, it will instead cause an adverse effect that the bad smell is stronger.

Accordingly, how to solve the aforementioned issues and shortcomings of the prior art is a trend for research and development by the present inventor and related vendors.

SUMMARY OF THE INVENTION

The primary object of the present invention is to provide an aromatic deodorant which is primarily constituted by a first cover, a second cover and a scent device, wherein an interior of the first cover is extended outward with a fixing element, an interior of the second cover is extended outward with a fixing seat to pivot the fixing element, the scent device is transfixed at the fixing element and is fixed by the fixing seat, and a scent which is released by the scent device is dissipated by air convection to an outer space through air vents formed on the first cover. When a user needs to stop releasing the scent, he or she only needs to rotate the first cover and the second cover through pivoting of the fixing element and the fixing seat and uses an isolation plate on the second cover to block the air vent to stop the scent. As a result, the user can easily control an extent of the scent in a space where the bad smell needs to be removed, depending on a personal requirement to a concentration of the scent.

Another object of the present invention is to provide an aromatic deodorant that through the aforementioned structures, the aromatic deodorant can be put in any space where the bad smell needs to be removed without taking up space, which is extremely convenient in usage.

Still another object of the present invention is to provide an aromatic deodorant which will not allow the scent to be attached on a hand when being accessed by the user, so as to keep clean.

To enable a further understanding of the said objectives and the technological methods of the invention herein, the brief description of the drawings below is followed by the detailed description of the preferred embodiments.

DETAILED DESCRIPTION OF THE PREFERRED EMBODIMENTS

Figure 1:
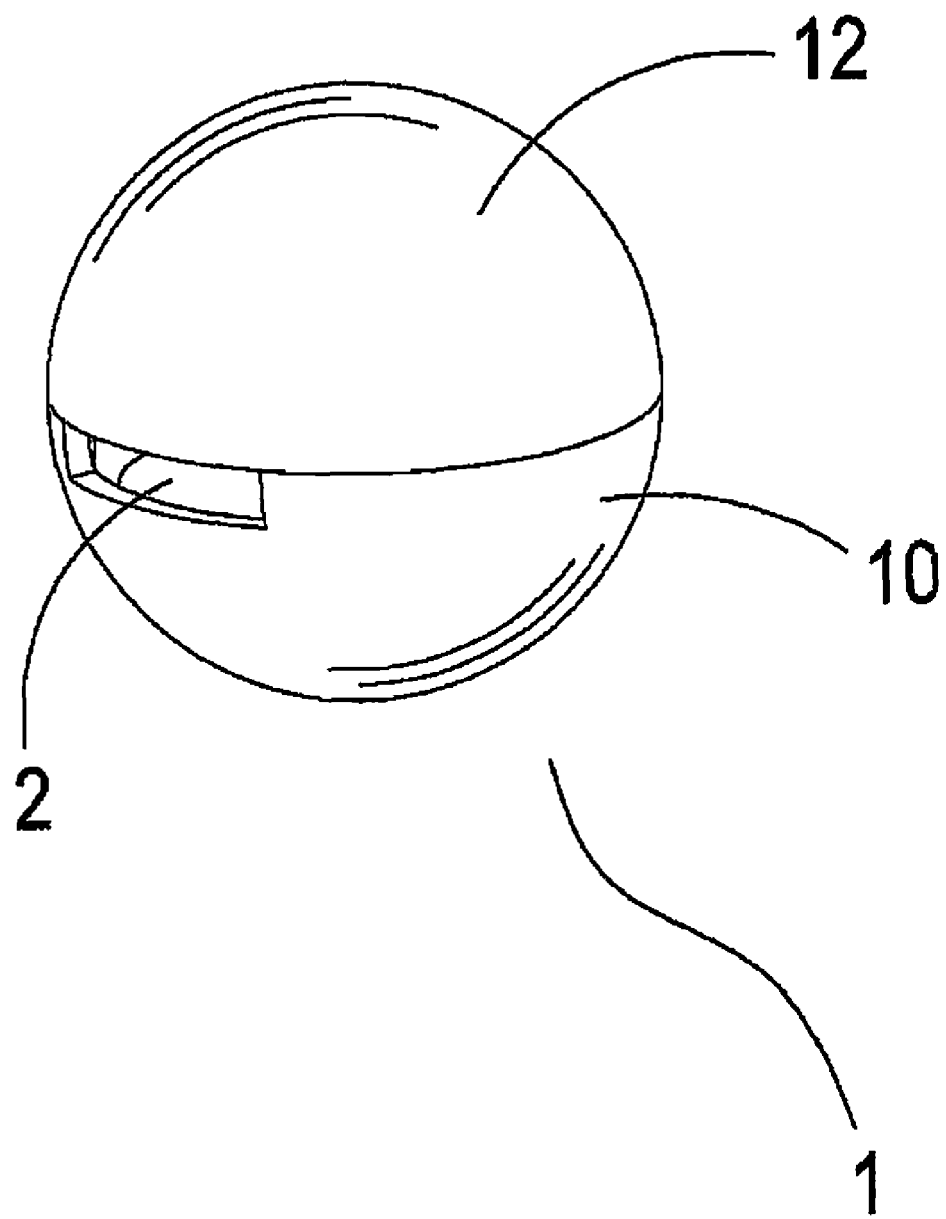
FIG. 1 shows a three-dimensional schematic view of a preferred embodiment of the present invention.
Figure 2:
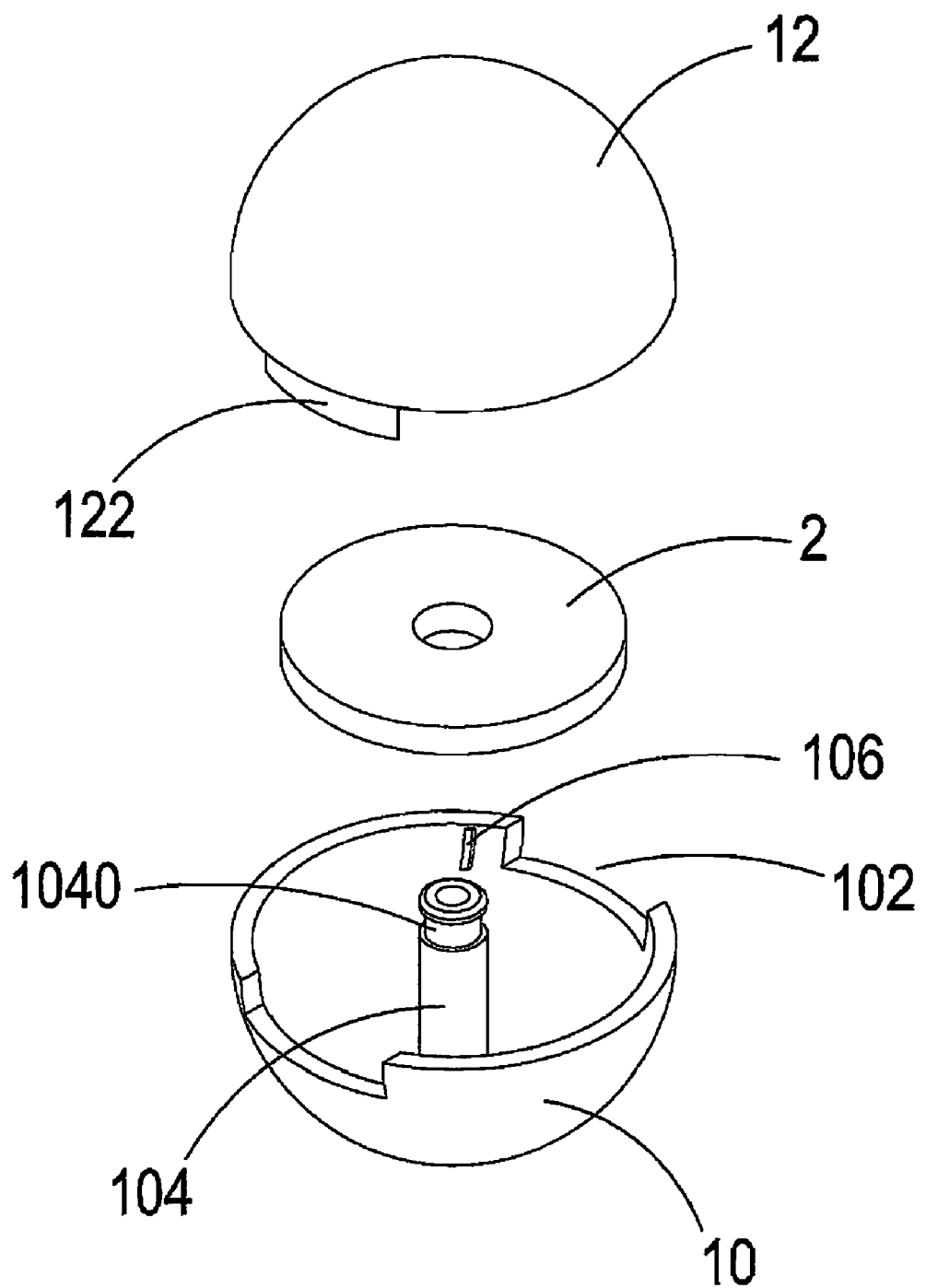
FIG. 2 shows a first three-dimensional exploded view of a preferred embodiment of the present invention.
Figure 2A:
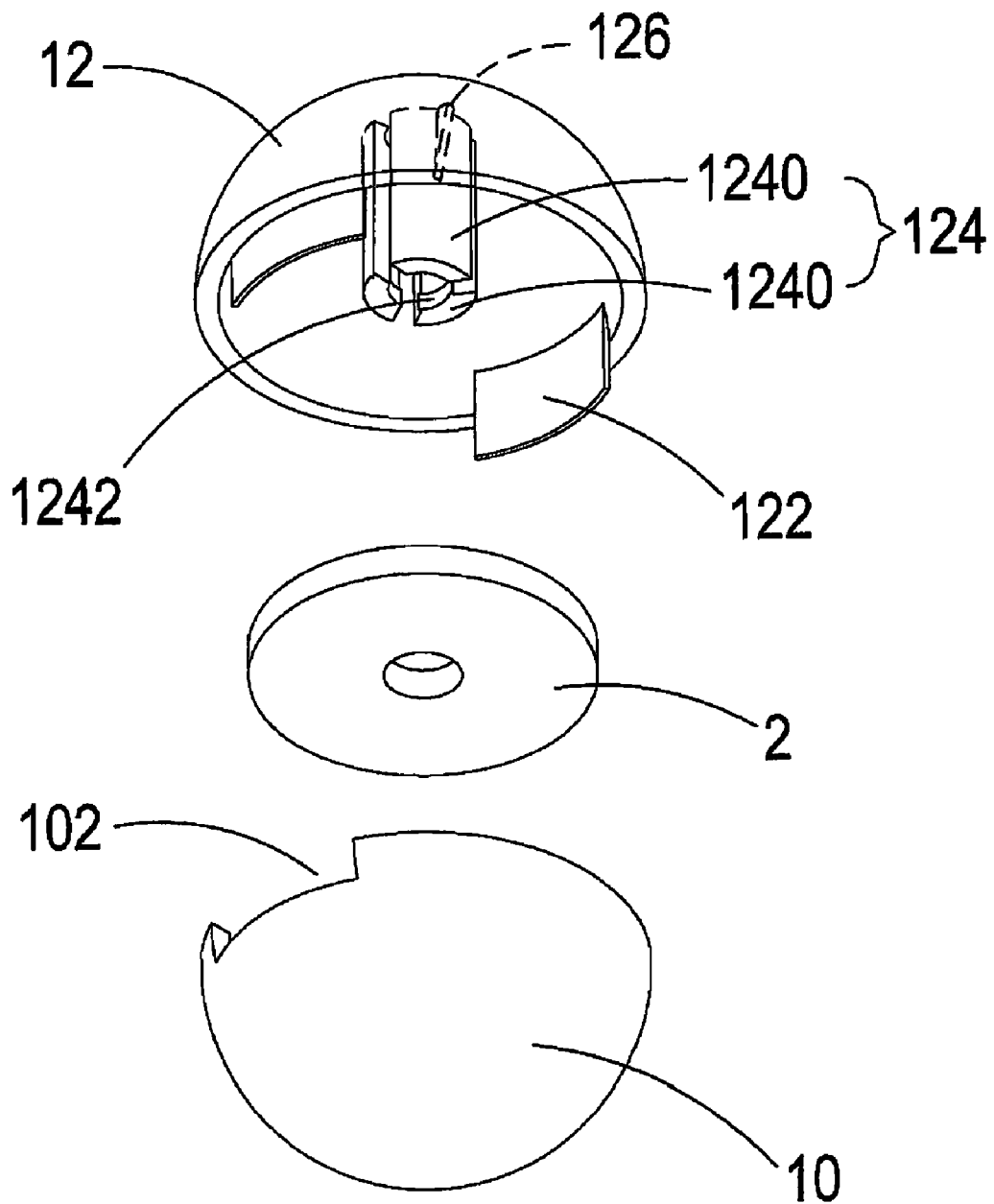
FIG. 2A shows a second three-dimensional exploded view of a preferred embodiment of the present invention.

Referring to FIGS. 1, 2 and 2A, it shows a three-dimensional schematic view, a first three-dimensional exploded view and a second three-dimensional exploded view, of a preferred embodiment of the present invention. As shown in the drawings, the present invention is an aromatic deodorant 1 which comprises primarily a first spherical cover 10, a second spherical cover 12 and a scent element 2, wherein pre-determined positions of the first spherical cover 10 are formed with air vents 102, an interior of the first spherical cover 10 is extended outward with a cylindrical pillar 104, the second spherical cover 12 is extended with an isolation plate 122 corresponding to the air vents 102, an interior of the second spherical cover 12 is extended outward with a fixing seat 124 which is formed by surrounding with plural fixing plates 1240, each having a fixing rib 126 respectively, and an end of the fixing element 104 that is far away from the first cover 10 is formed with an annular recess 1040. On the other hand, an end of each fixing plate 1240 that is far away from the second spherical cover 12 is formed respectively with a locking part 1242 which is engageable with the annular recess 1040. By pivoting the fixing plate 1240 and the fixing seat 124, the first spherical cover 10 can rotate with respect to the second spherical cover 12 and a positioning member 106 formed adjacent to the air vents 102 provides for the isolation plate 122 to be abutted and for fixing a position of the isolation plate 122; whereas, the scent element 2 is transfixed at the cylindrical pillar 104 and is fixed by the fixing seat 124, and a scent which is dissipated by the scent element 2 is released to an outer space by convection through the air vents 102 formed on the first spherical cover 10.

Figure 3:
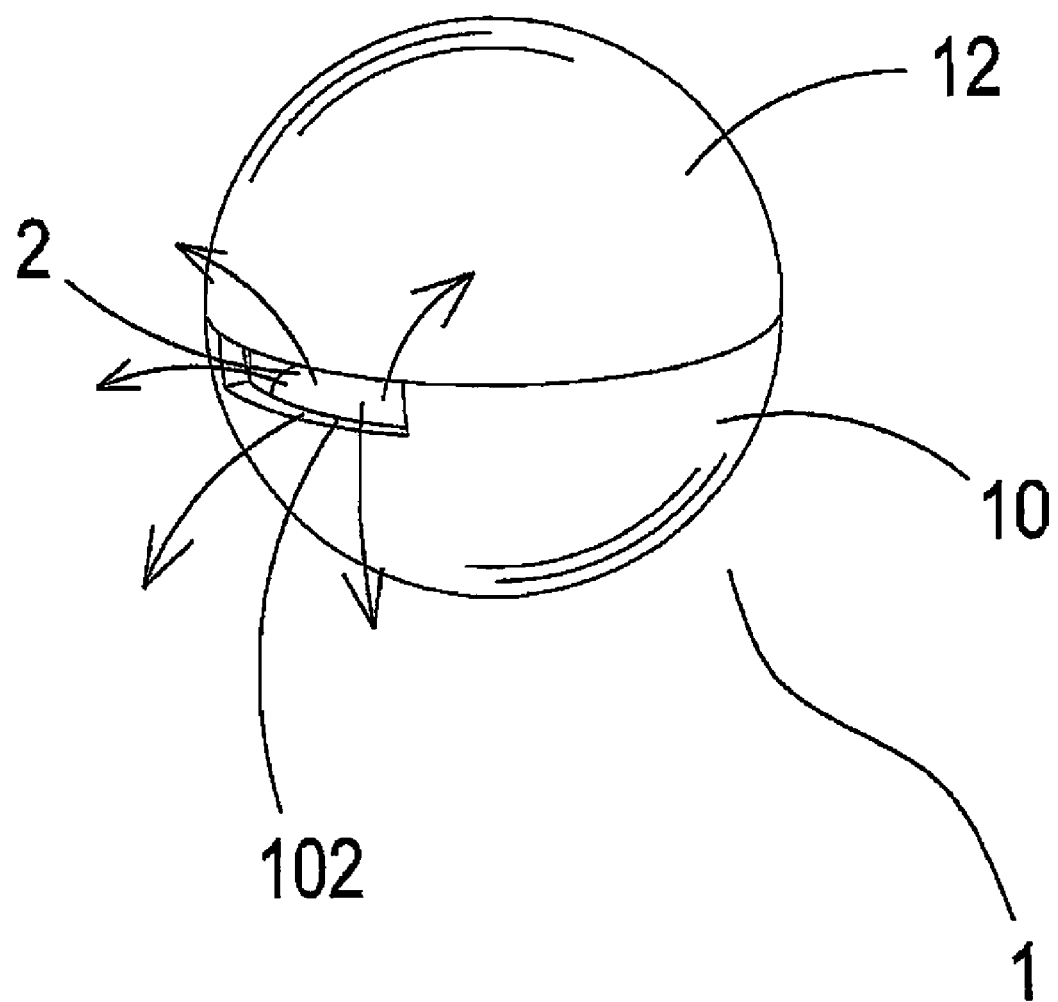
FIG. 3 shows a three-dimensional schematic view of the present invention wherein a scent is circulated through air vents.
Figure 4:
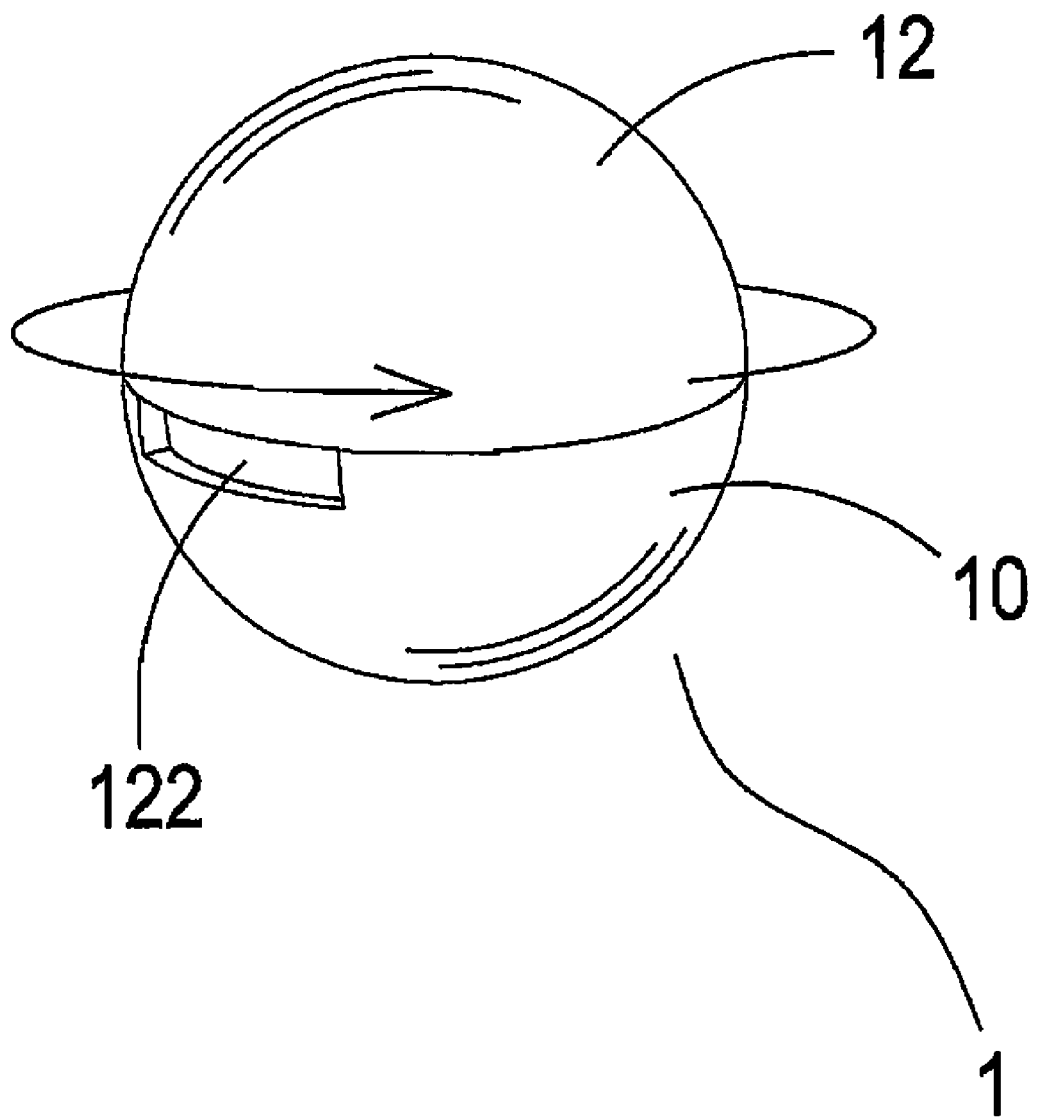
FIG. 4 shows a three-dimensional schematic view of the present invention wherein gas is blocked.

Referring to FIG. 3 and FIG. 4, it shows a three-dimensional schematic view of the present invention wherein a scent is circulated through air vents and a three-dimensional schematic view of the present invention wherein gas is blocked. As shown in the drawings, in association with FIG.

2 and FIG. 2A as a same time, as the scent element 2 is transfixed at the cylindrical pillar 104 and is fixed by the fixing seat 124, the scent can be distributed uniformly in the deodorant 1, and the pre-determined positions on the first spherical cover 10 are formed with the air vents 102 which allow air to be circulated. Therefore, the scent which is dissipated by the scent element 2 will be drifted away following the air circulation. Accordingly, when this deodorant 1 is put in a shoe cabinet or a shoe which is full of a bad smell, a condition of the tangy bad smell can be quickly improved.

On the other hand, when the user takes the deodorant 1 out of the shoe and has to stop dissipating the scent, he or she only needs to use the pivoting of the cylindrical pillar 104 and the fixing seat 124, allowing the first spherical cover 10 to rotate with respect to the second spherical cover 12 until that the isolation plate 122 is abutted with the positioning member 106, which means that the air vents 102 have been completely blocked. At this time, the interior scent will not be dissipated outside again. Therefore, the user can easily control an extent of the scent in a space where the bad smell needs to be removed, depending on a personal requirement to a concentration of the scent.

Figure 5:
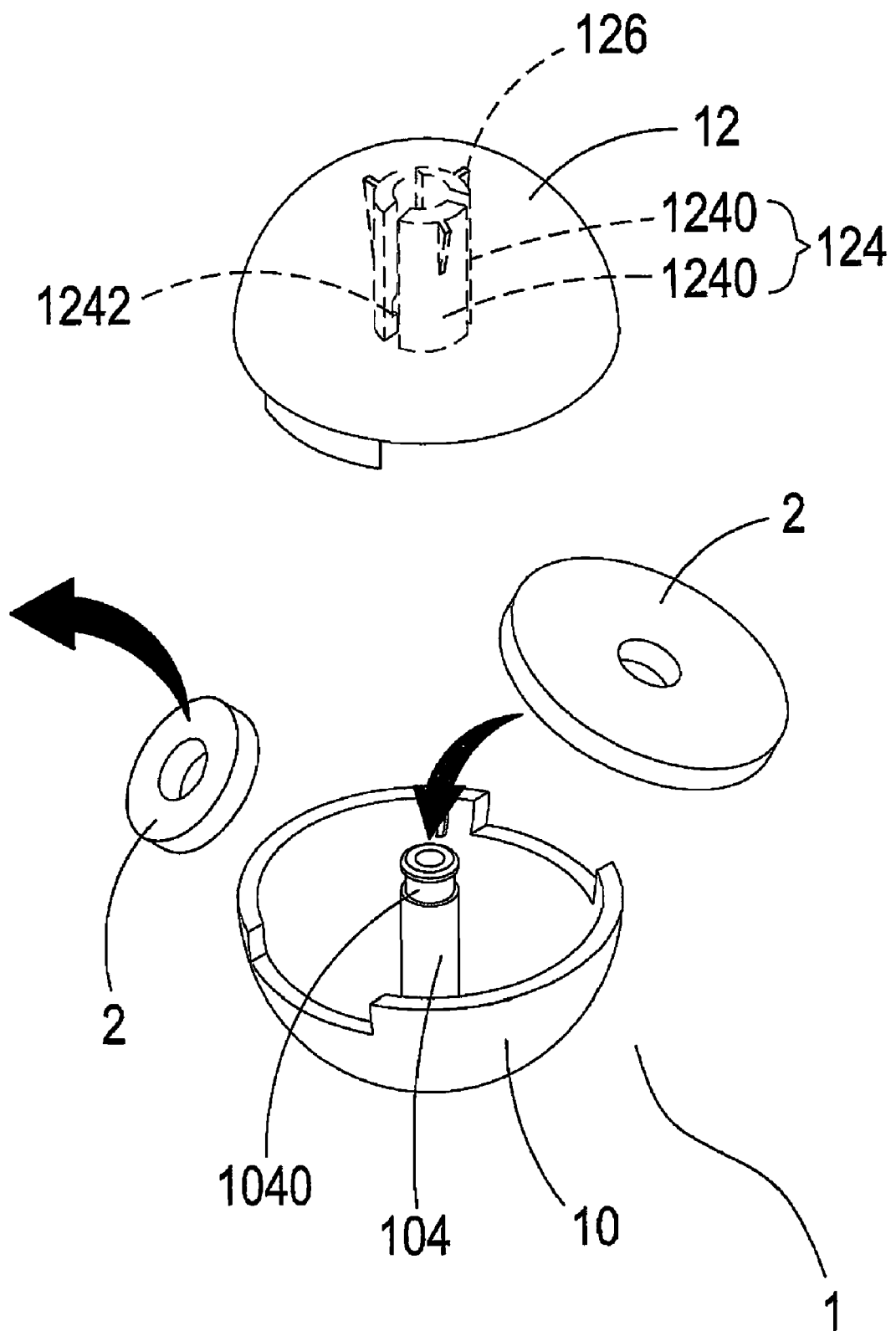
FIG. 5 shows a schematic view of assembling of the present invention wherein a scent device is being replaced.

Referring to FIG. 5, it shows a schematic view of assembling of the present invention wherein a scent device is being replaced. As shown in the drawing, when the scent element 2 in the deodorant 1 is to be replaced, the annular recess 1040 that is formed at one end of the cylindrical pillar 104 far away from the first spherical cover 10 is first dismantled from the locking parts 1242 formed on the ends of the fixing plates 1240 far away from the second spherical cover 12 and then the scent element 2 that is transfixed on the cylindrical pillar 104 is taken out. After a new scent element 2 has been installed, the cylindrical pillar 104 can be latched to the locking parts 1242 through the annular recess 1040, allowing the cylindrical pillar 104 to pivot the fixing seat 124. As each fixing plate 1240 is provided respectively with the fixing rib 126, when pivoting, a stress effect which is resulted to the fixing plates 1240 by the cylindrical pillar 104 can be intensified, so as to effectively avoid rupture which is caused when the deodorant 1 is used for a long time or is dismantled frequently.

Figure 6:
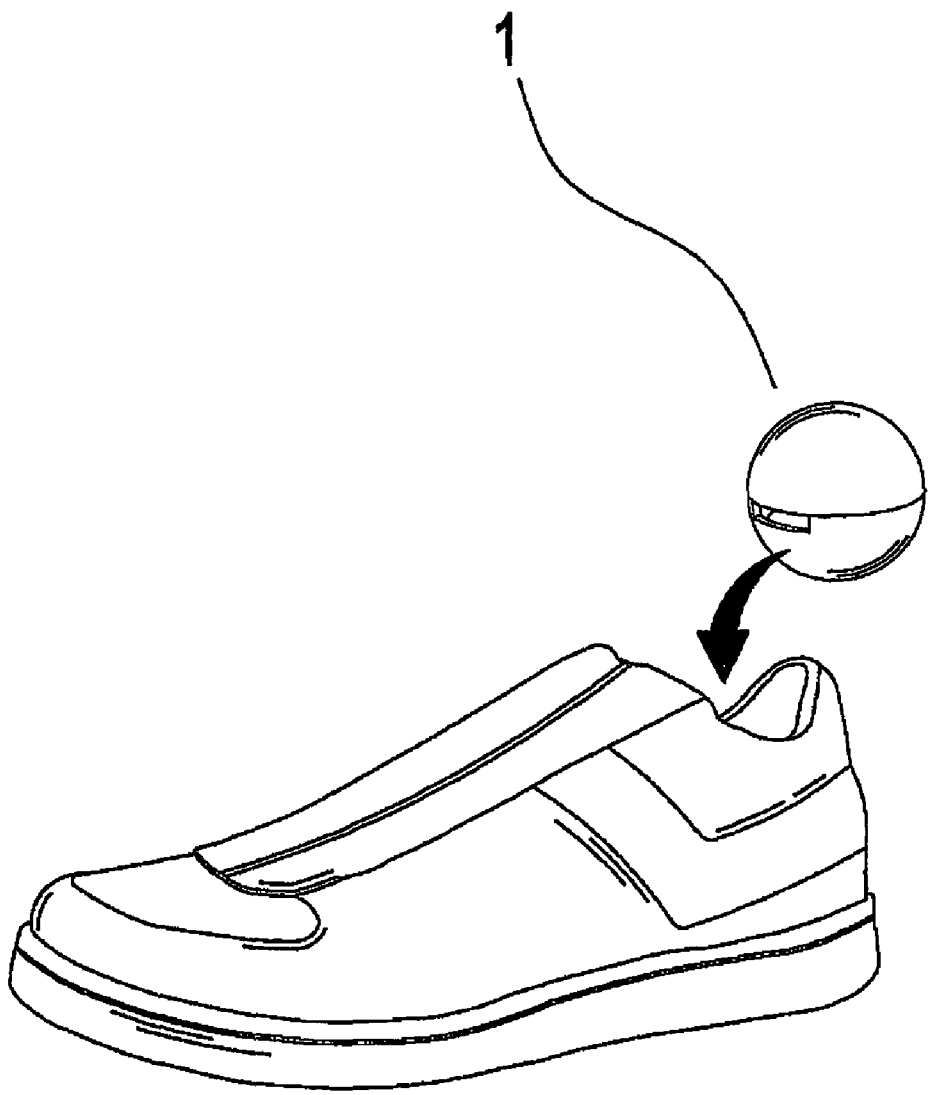
FIG. 6 shows a schematic view of a usage state of the present invention which is put in a shoe.

Referring to FIG. 6, it shows a schematic view of a usage state of the present invention which is put in a shoe. As shown in the drawing, as an entire structure of the deodorant 1 is small and is primarily in a rounded shape, it can rotate conveniently and can be easily put in a shoe to remove the bad smell. In addition, the deodorant 1 can be designed by various shapes of balls to draw attention of consumers, thereby improving a sales volume.

It is of course to be understood that the embodiments described herein is merely illustrative of the principles of the invention and that a wide variety of modifications thereto, such as adding a hanging rope to become an automobile decoration or an aromatic hanging decoration in a room or a lavatory, may be effected by persons skilled in the art without departing from the spirit and scope of the invention as set forth in the following claims.

What is claimed is:

1. An aromatic deodorant comprising:
   a first spherical cover having two air vents and a center provided with a cylindrical pillar, said cylindrical pillar extending outwardly from said first spherical cover, said cylindrical pillar having an outer end provided with an annular recess, said first spherical cover having an inner surface provided with a positioning member;
   a scent element having a center hole receiving said outer end of said cylindrical pillar;
   a second spherical cover adapted to engage with said first spherical cover, said second spherical cover having two isolation plates corresponding to said air vents of said first spherical cover, said second spherical cover having a center provided with a fixing seat extending outwardly from said second spherical cover, said fixing seat comprising three fixing plates which are arranged to form a passage between said three fixing plates thereby enabling said cylindrical pillar of said first spherical cover to be received in said passage and therefore causing said first spherical cover to be rotatable with respect to said second spherical cover, each of said fixing plates being provided with a locking part configured to be engageable with said annular recess of said first spherical cover;
   wherein when said first spherical cover is engaged with said second spherical cover, outer ends of said fixing plates of said fixing seat bear against said scent element thereby keeping said scent element in place and said locking parts of said fixing plates of said fixing seat are engaged with said annular recess of said first spherical cover; wherein when in use, said first spherical cover is rotated with respect to said second spherical cover to adjust opening of said air vents of said first spherical cover; and wherein when not in use, said first spherical cover is rotated with respect to said second spherical cover until one of said two isolation plates of said second spherical cover is abutted with said positioning member of said first spherical cover.

2. The aromatic deodorant as claimed in claim 1, wherein each of said fixing plates is provided with a rib for strengthening structure of said fixing plates.

* * * * *